July 29, 1975 R. L. BYRUM Plant Pat. 3,749
ROSE PLANT
Filed May 10, 1974
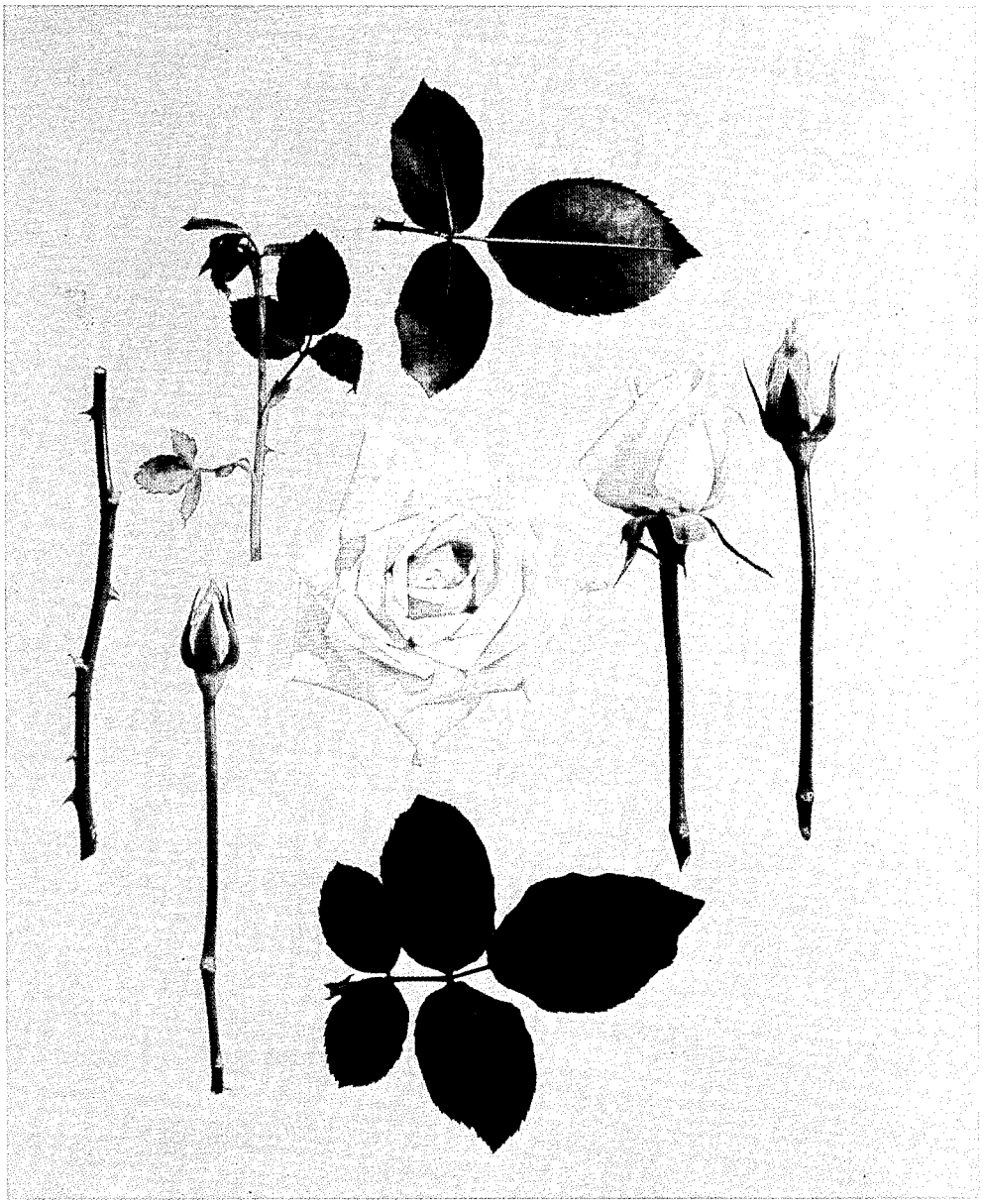

United States Patent

Plant Pat. 3,749
Patented July 29, 1975

3,749
ROSE PLANT

Roy L. Byrum, Richmond, Ind., assignor to
Joseph H. Hill Company, Richmond, Ind.

Filed May 10, 1974, Ser. No. 468,893
Int. Cl. A01h *5/00*
U.S. Cl. Plt.—18 1 Claim

ABSTRACT OF THE DISCLOSURE

A new variety of hybrid tea rose intended for greenhouse culture, distinguished by its continuous and abundant production of soft pink flowers of medium size borne on strong upright stems of medium length, particularly suited for the commercial trade because of their color compatibility in arrangements with allied flowers, the very attractive and unusual shape of the bud, and the longevity of the blooms as cut flowers.

BACKGROUND OF THE INVENTION

This new variety of rose plant originated as a seedling of Eternal Sun (P.P. 2,689) × Carina (P.P. 2,378), the crossing having been made by me at Richmond, Ind., in March 1966 in the course of breeding efforts being carried on by me with the object of developing new and improved rose varieties for the greenhouse production of cut flowers. This plant was discovered by me in October 1967 and was selected for propagation and test because of the lovely blush pink color of its beautifully formed flower and subsequent propagation of this plant by budding at Hamilton City, Calif., under my direction and through many generations has demonstrated that its novel color characteristic as well as other morphological and physiological advantages hereinafter described are firmly fixed and hold true from generation to generation.

DESCRIPTION OF THE DRAWING

My new rose plant is illustrated by the accompanying photographic drawing, in full color, which shows the buds in progressive stages of development, a face view of a fully opened flower, and the characteristics of the wood and the foliage, the colors of the buds and blossom being as nearly true as it is reasonably possible to obtain by conventional photographic procedures.

DESCRIPTION OF THE NEW PLANT

The following is a detailed description of this new variety of rose plant with color designations according to Robert Wilson's Horticultural Colour Chart (W) published by the Royal Horticultural Society of London, England, and according to Koster's Color Guide (K), all observations having been made at Richmond, Ind., where this new rose plant is grown in greenhouse.

The plant

Origin: Seedling (#67–13P).
Parentage:
*Seed parent.*—Eternal Sun (P.P. 2,689).
*Pollen parent.*—Carina (P.P. 2,378).
Classification: Hybrid tea.
Form: Bush, upright and branched.
Growth: Free and vigorous.
*Canes.*—Large and of medium diameter.
*Main stems.*—Color—(K) Ivy Green, Plate No. 83. Thorns: Several of medium length, downwardly hooked and with short base. Color: (K) Tobacco Brown, Plate No. 88.
*Branches.*—Color—(W) Spinach Green 0960/1. Thorns: Several of medium length, hooked downward and with short base. Color: (W) Rhodonite Red 0022/3 changing to Sap Green 62/3 at tip.
Prickles:
Several. Color: (W) Rhodonite Red 0022/3.
*New Shoots.*—Color—(W) Scheeles Green 860/3. Thorns: Few. Short, downwardly hooked and with short narrow base. Color: Almost clear with a slight tinge of (W) Orient Pink 416/3.
Foliage: Quantity—Abundant.
*Leaves.*—Shape—Compound; odd pinnate with 3 to 5 leaflets. Size—Large.
*Leaflets.*—Shape: Ovoid with obtuse to mucronate apex, round base and simply serrate margin. Texture: Heavy and leathery. Color: Young leaflets: Upper surface—(W) Lettuce Green 861/3 washed with Oxblood Red 00823. Under surface—(W) Oxblood Red 00823/3. Mature leaflets: Upper surface—(W) Spinach Green 0960 (nearest color). Under surface—(K) Cedar Green, Plate No. 80 (nearest color).
*Rachis.*—Heavy with grooved upper side and prickley under side.
*Stipules.*—Turning out at less than 45° from stem. Shape: Short and of medium width with short points.

The bud

Before calyx breaks:
*Size.*—Medium large.
*Form.*—Ovoid, with conspicuous neck and foliaceous appendages on the surface of the bud with parts extending beyond tip of the bud at least one-quarter of the bud length.
*Color of calyx.*—(W) Scheeles Green 860/3.
As calyx breaks:
*Color of Bud.*—(W) Porcelain Rose 620/1.
As first petals open:
*Size.*—Medium large.
*Form.*—Long pointed. Bud opens to shape of a brandy snifter glass as petals begin to unfurl.
*Color of petals.*—Outside—(W) Mandarin Red 17/3. Inside—(W) Mandarin Red 17/2.
Opening rate: Bud opens well in greenhouse.
Sepals: Permanent, spear shaped and of medium length.
*Color.*—Inside—(W) Scheeles Green 860/1 overlaid with white fuzz. Outside—(W) Scheeles Green 860/1.
Peduncle: Short, large diameter, strong and erect.
*Bark.*—Smooth, with color of (W) Scheeles Green 860. No thorns, prickles or hairs.

The flower

Blooming habit: Abundant and continuous.
Borne: Singly on strong stems of medium length.
Size: Medium large (when fully open), 3½ to 4 inches in diameter.
Shape: Full and high centered with petals tightly rolled outward, becoming high centered with petals loosely rolled outward at maturity.
Petalage: Very double with 45 to 50 petals, regularly arranged.
*Shape.*—Ovate, with obtuse apex. Some inside petals have one notch.
*Texture.*—Moderately thick.
*Appearance.*—Inside—Satiny. Outside—Shiny.
*Persistence.*—Petals hang on.
*Color.*

*Newly opened flower*

Outside petals: Outer surface—(W) Porcelain Rose 620/3 gradually changing to Primrose Yellow 601/3 at base. Inside surface—(W) French Rose 520/1 gradually changing to Primrose Yellow 601/2 at base.

Intermediate petals: Outside surface—(W) French Rose 520/2 with base almost white. Inside surface—(W) French Rose 520/1 with Primrose Yellow 601/3 at base.

Inner petals: Outside surface—(W) French Rose 520/2 with base almost white. Inside surface—(W) French Rose 520/1 with base almost white.

*Flower opened three days*

Outside petals: Outside surface—(W) Rose Pink 427/2 at top of petal changing through Rose Pink 427/3 to almost white at base. Inside surface—(W) Rose Pink 427/1 at top of petal with Primrose Yellow 601/3 at base.

Intermediate petals: Outside surface—(W) Rose Pink 427/2 gradually changing to almost white at base. Inside surface—(W) Rose Pink 427/1 with Primrose Yellow 601/3 at base.

Inner petals: Outside surface—(W) Rose Pink 427/2 gradually changing to almost white at base. Inside surface—(W) Rose Pink 427/1 with Primrose Yellow 601/3 at base.

General color effect of open bloom:

*Newly opened flower.*—(W) French Rose 520/2.

*Three days open.*—(W) French Rose 520/2.

Fragrance: Moderate tea (in greenhouse).

Lasting quality: 5 to 6 days as cut flower (July 1973).

Reproductive organs

Stamens: Many in number arranged regularly about the pistils.

*Anthers.*—Medium in size, all open at once. Color: (W) Orange Buff 507/2.

*Filaments.*—Length—Medium. Color: (W) Rose Opal 022/1.

*Pollen.*—Abundant, (W) Orange Buff 507/1 in color.

Pistils: Many in number.

*Styles.*—Uneven—medium length, moderately thin and bunched. Color: (W) Spinel Pink 0625/1.

*Stigmas.*—(K) Pure White, Plate No. 1, in color.

Ovularies: Some protruding from calyx.

Hips: None.

Seeds: None.

This new rose plant variety is completely different and is much better in color than its seed parent in that it is of a soft pleasing blush pink and better adapted to the commercial trade, whereas the seed parent is more novel in nature. The new plant is an improvement over its pollen parent in that its flowers are borne on stronger upright stems and are larger in size, especially in hot weather, and the plant does not slow down in winter months. In addition to the free growing habits of this new plant, the predominate distinctive features reside in the unusual shape of the bud, as shown in the drawing, the soft pink coloration of the flower, and its 5 to 6 day vase life as a cut flower.

The claim:

1. A new and distinct variety of rose plant substantially as herein shown and described, characterized by the soft pink color of the flowers and its free growing habits which provide a continuous and abundant year around production of blooms borne on strong erect stems.

No references cited.

ROBERT E. BAGWILL, Primary Examiner